United States Patent
Nord et al.

(10) Patent No.: US 7,817,778 B2
(45) Date of Patent: Oct. 19, 2010

(54) INTERACTIVE TREATMENT PLAN OPTIMIZATION FOR RADIATION THERAPY

(75) Inventors: Janne Ilmari Nord, Espoo (FI); Jarkko Yrjana Peltola, Tuusula (FI)

(73) Assignee: Varian Medical Systems International AG, Zug (CH)

( * ) Notice: Subject to any disclaimer, the term of this patent is extended or adjusted under 35 U.S.C. 154(b) by 127 days.

(21) Appl. No.: 12/201,785

(22) Filed: Aug. 29, 2008

(65) Prior Publication Data

US 2010/0054411 A1 Mar. 4, 2010

(51) Int. Cl.
*A61N 5/10* (2006.01)
(52) U.S. Cl. .................................................. 378/65
(58) Field of Classification Search .................... 378/65
See application file for complete search history.

(56) References Cited

U.S. PATENT DOCUMENTS 6,385,477 B1 * 5/2002 Werner et al. ................. 378/65
2003/0219098 A1 * 11/2003 McNutt et al. ................ 378/65

* cited by examiner

*Primary Examiner*—Chih-Cheng G Kao
(74) *Attorney, Agent, or Firm*—Townsend and Townsend and Crew LLP

(57) ABSTRACT

An interactive method for radiation treatment planning is disclosed. The method applies to staged treatment planning algorithms, as used, for example, with arc therapy. It allows the user to hold the optimization algorithm at a stage in order to make adjustments to the objective function before advancing to the next stage. If adjustments are made, the user can revert to an earlier stage and re-run the optimization process using the adjusted objective function. While a hold is imposed, the treatment planning software may continue optimization at the current stage.

8 Claims, 1 Drawing Sheet

INTERACTIVE TREATMENT PLAN OPTIMIZATION FOR RADIATION THERAPY

FIELD OF THE INVENTION

The present invention relates to treatment planning for radiation therapy, and is particularly useful in connection with staged treatment planning for arc therapy.

BACKGROUND OF THE INVENTION

In general, radiation therapy or radiotherapy, uses a beam of ionizing radiation to treat living tissue, usually a tumor. As used herein, the term radiotherapy should be broadly construed and is intended to include various techniques used to irradiate a patient, including use of either photons (such as high energy x-rays and gamma rays) or particles (such as electron and proton beams), and applies to both therapeutic and radiosurgical applications. For purposes of the present invention, the processes of treatment planning and administering the radiation to a patient can be generalized regardless of the type of radiation used.

Modern radiation therapy techniques include Intensity Modulated Radiotherapy ("IMRT"), volumetric modulated arc therapy (where the system gantry moves while radiation is delivered) and three-dimensional conformal radiotherapy ("3D conformal" or "3DCRT"). These techniques are typically implemented using a radiotherapy system, such as a linear accelerator, equipped with a multileaf collimator ("MLC"). While modern linear accelerators use MLCs, other methods of providing conformal radiation to a target volume are known and are within the scope of the present invention. Use of multileaf collimators in general, and arc therapy and IMRT techniques in particular, allow the radiologist to treat a patient from multiple angles while varying the shape and dose of the radiation beam, thereby providing greatly enhanced ability to deliver radiation to a target within a treatment volume while avoiding excess irradiation of nearby healthy tissue. The greater freedom which IMRT, arc therapy and other complex radiotherapy techniques provide has made the task of developing treatment plans more difficult.

Treatment planning typically starts with (1) images of the treatment volume (e.g., from CT or MRI scans) and, (2) the desired dose of radiation which is to be delivered to various portions of a target, such as a tumor, and (3) the maximum dose which can be safely absorbed by tissue structures, such as organs, within the treatment volume that are adjacent to or near the tumor or other target volume. As used herein, the term "treatment volume" is used to refer to the entire volume that will be subjected to radiation, and is sometimes referred to as the "irradiated volume." The target volume is intended to receive a therapeutic prescribed dose, and is sometimes referred to as the "planning target volume" ("PTV"). Thus, the target volume is within the treatment volume. Both the target volume and any nearby organs within the treatment volume may have complex three dimensional shapes compounding the difficulty of preparing a treatment plan.

The patient specific treatment planning information (e.g., volume boundaries, desired dose, etc.) is used to define or determine an objective function (sometimes referred to as a "cost function") that is then used in the treatment planning process. Thus, the typical objective function incorporates patient specific information comprising a combination of empirical data and prescribed dose information and limitations. More specifically, the objective function typically contains what are referred to as dose volume histogram ("DVH") constraints. The DVH constraints define both how much radiation is required in the various portions of the target volume, as well as limits on radiation in the remaining portions of the treatment volume outside the target volume. For example, a DVH constraint may specify that a certain structure not receive more than A dose in B % of the structure's volume; or it may specify that a tumor should receive at least x dose in y % of the tumor volume. There may be many DVH constraints in the objective function. The objective function may reflect tradeoffs arising due to the need to adequately irradiate a tumor, on one hand, and to protect surrounding tissue, on the other. The proper tradeoff or balance between these competing goals may not be clear at the outset of the process. Likewise, it may not be clear at the outset whether or how the treatment planning software can accommodate competing goals.

A variety of optimization algorithms have been developed to use the objective function to solve the "inverse problem" of devising and optimizing a specific, three-dimensional treatment plan for irradiating the treatment volume from a variety of angles (or, in arc therapy, while the system gantry is moving), in order to deliver a desired radiation dose to the target while minimizing irradiation of nearby tissue. The treatment plan preferably also takes into account the capabilities and physical limitations of the radiotherapy system to be used. Generally speaking, the inverse problem involves optimizing the selection of angles, the selection of MLC leaf movements and the durations of irradiations in accordance with the constraints of the objective function. Because of the large number of variables involved and complex matrix manipulations that are required, the optimization algorithms for calculating treatment plans require substantial computational time even when using modern high speed computers. These problems are even more difficult in treatment planning for arc therapy, which uses a moving source of radiation.

Generally two types of algorithms are used in treatment planning: (1) dose calculations algorithms based on a given set system parameters, e.g., gantry angle, MLC leaf positions, etc., and (2) search algorithms which use various techniques to adjust system parameters between dose calculations to achieve optimization of the plan. Some exemplary dose calculation algorithms include various Monte Carlo ("MC") techniques and pencil beam convolution ("PBC"). Some exemplary search algorithms include various stochastic and deterministic methods, including various simulated annealing ("SA") techniques, algebraic inverse treatment planning ("AITP"), and simultaneous iterative inverse treatment planning ("SIITP"). Such techniques, and others, are well known in the art, and each of the techniques has advantages and disadvantages relative to the others. Each of the methods requires iterative dose calculations for optimization, and generally a high number of dose calculation iterations or "passes" are required to converge on an optimal plan. Typically, each iteration involves changing the boundary conditions using the search algorithm and recalculating the dose distribution. While a fully optimized plan might be achieved using known methods if adequate time is available, as a practical matter time constraints often limit the ability to achieve this goal.

It is noted that a treatment plan is typically implemented over a time period. Thus, the patient typically is given multiple treatments over the course of days or weeks, such that the dose delivered to the treatment volume is fractionated. During the time between treatments changes may occur in the treatment volume, for example, the tumor being irradiated may shrink in size or surrounding organs may change position. Any such changes may necessitate revising and re-optimizing the treatment plan before the next fractionated dose or "fraction" is delivered. The problem of re-optimizing a treatment plan is known, and presents somewhat different issues than achieving an initially optimized plan as described herein. Since the use of fractions does not otherwise affect the treatment planning process, it is not necessary to discuss it in further detail.

Treatment planning algorithms may be implemented as part of an overall, integrated treatment planning software package which provides additional features and capabilities. For example, a dose calculation algorithm and search algorithm may be used to optimize a set of fluence maps at each gantry angle, with a separate leaf sequencer used to calculate the leaf movements needed to deliver them. Alternatively, a dose calculation algorithm and search algorithm may be used to directly optimize leaf movements and other machine parameters. The Eclipse™ Treatment Planning System offered by the assignee of the present invention includes such an integrated software program.

BRIEF SUMMARY OF THE INVENTION

A goal of the present invention is to increase the speed and efficiency of the treatment planning process. A further goal of the invention is to provide additional user control in the treatment planning process so that improved results can be achieved.

In one aspect the present invention is directed to a tangible medium having treatment planning software stored thereon, the software comprising one or more algorithms for optimizing a treatment plan in stages according to a preprogrammed schedule based on an objective function including patient specific information, said software having an interactive mode, wherein said interactive mode comprises code for holding the optimization process at a user-selected stage until receiving user instructions, code for accepting user adjustments to the objective function while the optimization process is underway; and code for restarting the optimization at a user-selected stage after adjustments have been made to the objective function. The software may further include code for revising the preprogrammed schedule and for adjusting the objective function while the optimization process is underway without imposing a hold. The code may provide for holding the optimization process at a user-selected stage permits continued optimization at that stage while awaiting user instructions.

In another aspect the present invention is directed to a method of treatment planning for radiotherapy using interactive treatment planning software having one or more optimization algorithms, comprising, defining an initial objective function comprising a plurality of fields including fields comprising patient specific information, dividing the optimization process into a plurality of sequential stages, wherein fields are added to the optimization process at different stages according to a preprogrammed schedule unless a hold is imposed, holding the optimization process in response to user request, and after the user hold is imposed, continuing the optimization process at the current stage until receiving further instructions. The method may further include the step of adjusting the objective function after the hold has been imposed and proceeding with optimization using the adjusted objective function. The method may also include the step of reverting to an earlier stage after the objective function has been adjusted. The method may further include making further a adjustment to the objective function after evaluating the results attained after making the initial adjustment.

DETAILED DESCRIPTION OF THE INVENTION

Figure 1:
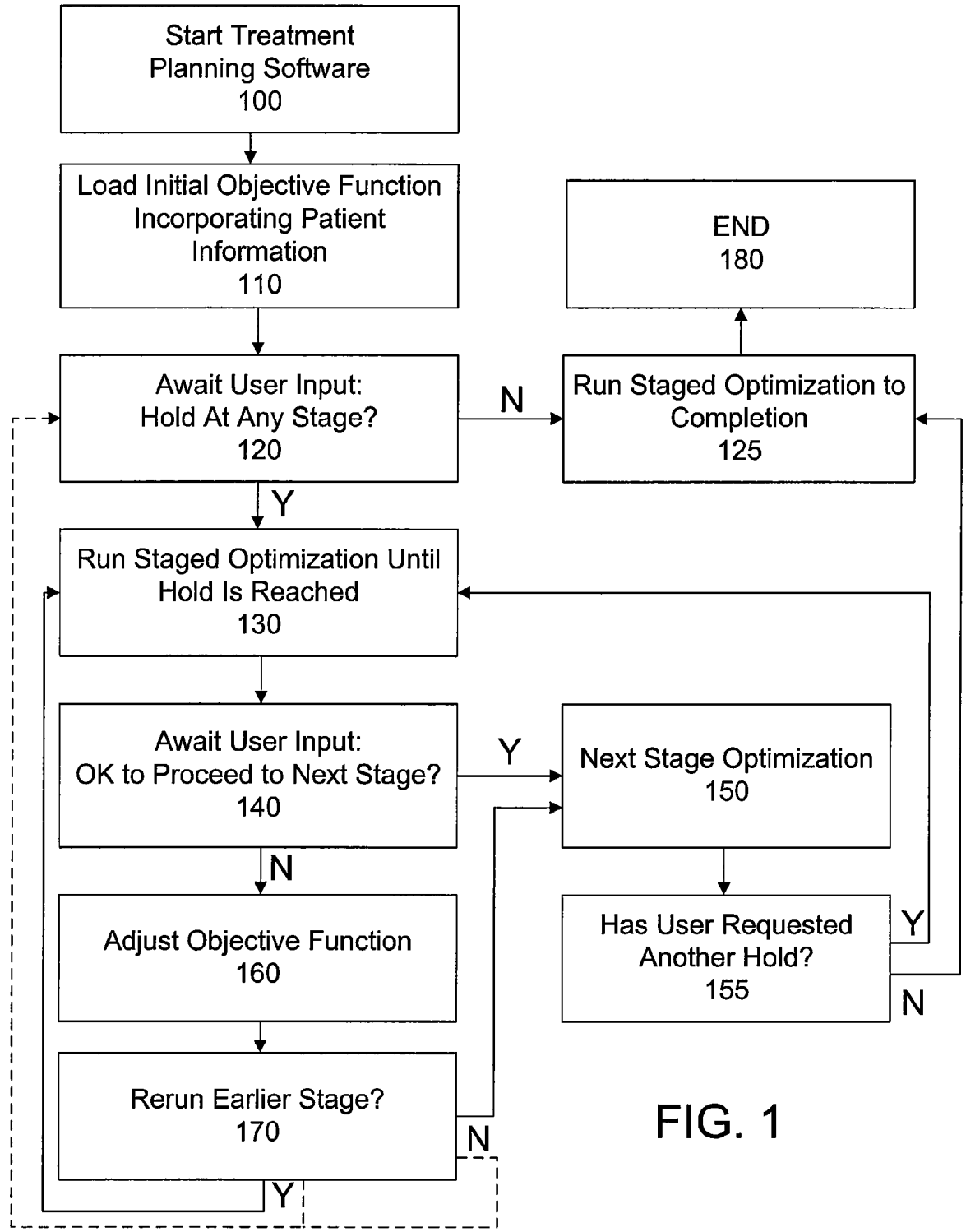
FIG. 1 is a flow chart of a method in accordance with one embodiment of the present invention.

As described above, treatment planning for radiotherapy seeks to inform the radiologist or other operator of the radiotherapy system how to deliver a prescribed fractional dose of radiation to a target volume, such as a tumor, while minimizing the radiation dose to surrounding tissue in the treatment volume, taking into account the capabilities of the radiotherapy system such as beam energy, beam fluence etc. Moreover, modern radiotherapy systems use sophisticated beam shaping structures, typically multileaf collimators ("MLCs"), to precisely control the shape of the radiation beam from any selected angle, and that can also be used to vary the beam strength using IMRT. Arc therapy, one of the newest techniques for radiotherapy, involves moving the gantry while delivering radiation. In addition, modern systems can control beam fluence in real time. Sophisticated treatment planning software can interface directly with the radiotherapy system, generating machine language instructions to the system for implementing the treatment plan. For example, such treatment planning software will calculate and generate machine control signals for moving the leaves of the system MLC and the system gantry, and for adjusting the beam strength.

Because of the complexity of the problem, treatment planning typically uses an optimization algorithm to converge on a final plan based on an objective function which comprises patient information including, for example, dose volume histogram (DVH) information and constraints. The objective function also comprises information about the capabilities of the radiotherapy system that will be used to administer the treatment plan. Usually, the objective function describes how close the plan is to the desired dose distribution, taking into account the DVH information and constraints. As described above, the objective function may involve tradeoffs between competing objectives.

Treatment planning software, particularly when used for arc treatment optimization, proceeds in stages. At the outset of the optimization process, only a few fields are used, and as optimization progresses more fields are added in a preprogrammed schedule. Typically, the progression from one stage to the next is based on a prescribed number of iterations or "passes," a prescribed amount of time, or a prescribed amount of convergence of the objective function. In practice, a particular stage is not fully optimized before proceeding to the next stage. As used herein, proceeding to the next stage refers generally to the addition of one or more of the fields in the objective function into the optimization process. Accordingly, stages may be thought of as corresponding to levels accuracy, with the optimization process progressing with greater accuracy as it progresses from stage to stage. Different stages have different responsivity to different optimization objectives. Heretofore, this general approach has not allowed users to make adjustments to the objective function or to the preprogrammed schedule once optimization has begun.

The present invention provide users with the ability to interact with the optimization routine as it progresses. Specifically, the inventors have determined that improved treatment planning results can be obtained if the user can make adjustments to the objective function as optimization proceeds. In its broad form, the present invention allows users to monitor the progress of treatment planning optimization and to evaluate and change the objective function throughout the optimization process. Specifically, the invention allows monitoring of the solution as the treatment planning optimization process continues and allows the user to react by making changes to the objective function. After changing the objective function, the user can either allow optimization to proceed per the original staged schedule or can restart at an earlier stage using the changed objective function.

For example, as noted optimizing the treatment plan may involve tradeoffs between treating cancerous tissue and protecting healthy tissue. An objective function may start with the goal of saving both of the patient's parotids while providing a specified radiation dose to an adjacent tumor. In the course of running the optimization program it may become apparent that this cannot be accomplished due to the target geometry. According to the interactive treatment planning method of the present invention, the user may then decide to change the objective function in the midst of the optimization process to specify that only the right parotid should be saved. After running the optimization program further using the modified objective function it may become clear that the right parotid cannot be saved. The user may then again revise the objective function; this time to specify that only the left parotid be saved. In each instance the user may specify that the operation of the program should be held at the current stage while changes to the objective function are made and evaluated. Moreover, after changes are made to the objective function, the user may specify the starting stage for continued running of the optimization program. In our example, after entering the second round of changes to the objective function and running the program further, it may be determined that there is a solution (i.e., a treatment plan) which allows the left parotid to be saved. In such a case, the outcome of user interaction—saving one parotid—is preferable to the initial but unattainable goal of trying to save both.

FIG. 1 is a flow chart of according to one embodiment of the present invention. The treatment planning software program is started (step 100) and the objective function is loaded (step 110). The treatment planning software includes a staged optimization routine that is preprogrammed. The preprogrammed routine may be user adjustable and may be entered before or after the objective function is loaded. The program then pauses to await user instructions specifying whether the program should hold at any stage (step 120). If no hold is requested, the staged optimization program proceeds normally to completion (steps 125, 180) according to the preprogrammed schedule. If one or more holds are requested the program runs normally until the first hold is reached (step 130). At that time the program does not proceed to the next stage until further user input (step 140), but may continue optimizing at the current stage as described above. The user may then accept the results of the stage and proceed to the next stage (step 150), or the user may make one or more adjustments to the objective function (step 160). As used herein any combination of additions and/or modifications to the objective function is considered an "adjustment." After adjusting the objective function, the user instructs the system (step 170) to either continue to hold at the current stage for further evaluation using the adjusted objective function, proceed to the next stage (step 150) or to rerun an earlier stage (step 130), in either case using the changed objective function. If, at step 170, the software is instructed to proceed to the next stage, it then determines whether the user has requested another hold (step 155). If another hold has not been requested the program proceeds with staged optimization to completion (steps 125, 180). If another hold has been requested, the program repeats steps 130, 140, etc.; i.e., staged optimization continues until the next hold is reached and further user input is given. If, at step 170, the user specifies that a stage should be re-run, the software reverts to the earlier stage specified and proceeds until the next hold is reached (step 130). Optionally, after step 170 (or at any other point in the process) the program may pause for the user to add or delete holds.

In the embodiment of FIG. 1 the user specifies whether there should be a hold at the outset of the process (step 120). In an alternative embodiment, the user may monitor the optimization progress and request a hold at any time. While watching the progress of optimization, the user may determine that a different trade-off between the goals of the treatment plan could yield better results. Thus, for example, the user may wish to demand more or less of the plan. As in the embodiment of FIG. 1, requesting a hold does not require the user to modify the objective function. Rather the hold merely continues optimization at the present stage, allowing the user to observe and assess the results further before determining whether to adjust the objective function. If the objective function is adjusted, the user also specifies whether the program should continue to the next stage, re-run (or continue to run) the present stage, or revert to an earlier stage based on the adjusted objective function. After changing the objective function and specifying the point at which the program should continue, it takes some time for the optimizer to converge near the new solution. Typically, after several iterations, the user can evaluate whether the changes constitute an improvement and can either make further changes to the objective function or discard the changes and revert to the objective function as it existed before changes were made. On the other hand, if after imposing a hold the user decides that no change is necessary, the hold is released and the program proceeds to the next stage in accordance with the preprogrammed schedule. After releasing the hold, with or without adjusting the objective function, the user may thereafter continue to monitor the progress of optimization and impose another hold if warranted.

According to a further aspect of the interactive treatment planning method of the present invention, the user may also make changes to the objective function at any time without imposing a hold. This feature can be useful where the required change is small. In such cases, the change is made and the optimizer proceeds according to the preprogrammed schedule. Again, preferably the user can continue to monitor the progress of optimization and impose a hold if warranted.

Thus far, the invention has been described in connection with a preprogrammed schedule for moving from one stage to another, and this schedule is adhered to unless a hold is imposed by the user. According to another aspect of the interactive treatment planning technique of the present invention, the user can also make adjustments to this schedule during the optimization process. For example, the user may decide to add or subtract stages, or change the amount of time spent at a given stage as optimization proceeds.

The embodiments described above are illustrative of the present invention and are not intended to limit the scope of the invention to the particular embodiments described. Accordingly, while one or more embodiments of the invention have been illustrated and described, it will be appreciated that various changes can be made therein without departing from the spirit or essential characteristics thereof. Accordingly, the disclosures and descriptions herein are not intended to be limiting of the scope of the invention, which is set forth in the following claims.

What is claimed is:

1. A non-transitory tangible medium having treatment planning software stored thereon, said software comprising one or more algorithms for optimizing a treatment plan in stages according to a preprogrammed schedule based on an objective function including patient specific information, said software having an interactive mode, wherein said interactive mode comprises:

code for holding the optimization process at a user-selected stage until receiving user instructions;

code for accepting user adjustments to the objective function while the optimization process is underway; and code for restarting the optimization at a user-selected stage after adjustments have been made to the objective function.

2. The non-transitory tangible medium of claim 1, further comprising code for revising the preprogrammed schedule.

3. The non-transitory tangible medium of claim 1, further comprising code for adjusting the objective function while the optimization process is underway without imposing a hold.

4. The non-transitory tangible medium of claim 1, wherein said code for holding the optimization process at a user-selected stage permits continued optimization at that stage while awaiting user instructions.

5. A method of treatment planning for radiotherapy using interactive treatment planning software having one or more optimization algorithms, comprising:

defining an initial objective function comprising a plurality of fields including fields comprising patient specific information, dividing the optimization process into a plurality of sequential stages with software running on a computer, wherein fields are added to the optimization process at different stages according to a preprogrammed schedule unless a hold is imposed, holding the optimization process in response to user request, after the user hold is imposed, continuing the optimization process at the current stage until receiving further instructions.

6. The method of claim 5 further comprising the step of adjusting the objective function after the hold has been imposed and proceeding with optimization using the adjusted objective function.

7. The method of claim 6 further comprising reverting to an earlier stage after the objective function has been adjusted.

8. The method of claim 6 further comprising making further a adjustment to the objective function after evaluating the results attained after making the initial adjustment.

\* \* \* \* \*